United States Patent
Denker et al.

(10) Patent No.: US 7,519,421 B2
(45) Date of Patent: *Apr. 14, 2009

(54) VAGAL NERVE STIMULATION USING VASCULAR IMPLANTED DEVICES FOR TREATMENT OF ATRIAL FIBRILLATION

(75) Inventors: Stephen Denker, Mequon, WI (US); Cherik Bulkes, Sussex, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 630 days.

This patent is subject to a terminal disclaimer.

(21) Appl. No.: 11/112,181

(22) Filed: Apr. 22, 2005

(65) Prior Publication Data

US 2005/0187584 A1    Aug. 25, 2005

Related U.S. Application Data

(63) Continuation-in-part of application No. 10/197,191, filed on Jul. 17, 2002, now Pat. No. 6,907,285, which is a continuation of application No. 09/760,936, filed on Jan. 16, 2001, now Pat. No. 6,445,953.

(51) Int. Cl.
*A61N 1/39* (2006.01)
(52) U.S. Cl. .................... 607/5; 607/14; 607/33; 607/61; 607/122
(58) Field of Classification Search .............. 607/61, 607/116
See application file for complete search history.

(56) References Cited

U.S. PATENT DOCUMENTS

| | | | |
|---|---|---|---|
| 4,702,254 A | * | 10/1987 | Zabara ............... 607/45 |
| 5,170,802 A | | 12/1992 | Mehra |
| 5,405,367 A | * | 4/1995 | Schulman et al. ......... 607/61 |
| 5,411,535 A | | 5/1995 | Fujii et al. |

(Continued)

FOREIGN PATENT DOCUMENTS

WO      WO 2005/063332 A      7/2005

(Continued)

OTHER PUBLICATIONS

Schauerte et al., Transvenous Parasympathetic Nerve Stimulation in the Inferior Vena CAva and Atrioventricular Conduction, Journal of Crdiovascular Electrocphysiology, vol. 11, No.1, Jan. 2000.

(Continued)

*Primary Examiner*—Kennedy J Schaetzle
(74) *Attorney, Agent, or Firm*—George E. Haas; Quarles & Brady

(57) ABSTRACT

An abnormally rapid ventricular cardiac rate that results from atrial fibrillation can be reduced by stimulating a vagal nerve of the heart. An apparatus for such stimulation includes a power transmitter that emits a radio frequency signal. A stimulator, implanted in a blood vessel adjacent the vagal nerve, has a pair of electrodes and an electrical circuit thereon. The electrical circuit receives the radio frequency signal and derives an electrical voltage from the energy of that signal. The electrical voltage is applied in the form of pulses to the pair of electrodes, thereby stimulating the vagal nerve. The pattern of that stimulating pulses can be varied in response to characteristics of the atrial fibrillation or the ventricular contractions.

17 Claims, 3 Drawing Sheets

U.S. PATENT DOCUMENTS

| | | |
|---|---|---|
| 5,531,779 A | 7/1996 | Dahl et al. |
| 5,713,939 A | 2/1998 | Nedungadi et al. |
| 5,739,795 A | 4/1998 | Chanteau et al. |
| 5,741,316 A | 4/1998 | Chen et al. |
| 5,814,089 A | 9/1998 | Stokes et al. |
| 5,954,761 A | 9/1999 | Machek et al. |
| 5,995,874 A | 11/1999 | Borza |
| 6,026,818 A | 2/2000 | Blair et al. |
| 6,061,596 A * | 5/2000 | Richmond et al. ............ 607/41 |
| 6,067,474 A | 5/2000 | Schulman et al. |
| 6,138,681 A | 10/2000 | Chen et al. |
| 6,141,588 A | 10/2000 | Cox et al. |
| 6,431,175 B1 | 8/2002 | Penner et al. |
| 6,442,413 B1 | 8/2002 | Silver |
| 6,445,953 B1 | 9/2002 | Bulkes et al. |
| 2002/0005719 A1 | 1/2002 | Gilboa et al. |
| 2002/0026228 A1 | 2/2002 | Schauerte |
| 2002/0120304 A1 | 8/2002 | Mest |
| 2002/0128546 A1 | 9/2002 | Silver |
| 2002/0183791 A1 | 12/2002 | Denker et al. |
| 2005/0107847 A1 | 5/2005 | Gruber et al. |
| 2005/0131467 A1 | 6/2005 | Boveja |
| 2005/0187584 A1 | 8/2005 | Denker et al. |

FOREIGN PATENT DOCUMENTS

| | | |
|---|---|---|
| WO | WO 2005/107852 A | 11/2005 |

OTHER PUBLICATIONS

Schauerte et al., Ventricular Rate Control During Atrial Fibrillation by Cardiac Parasympathetic Nerve Stimulation: A Transvenous Approach, Jounal of the Am. College of Cariaology. vol. 34, No. 7, 1999.

DiMarco, Selective Vagal Nerve Stimulation for Rate Control in Atrial Fibrillation, American Medical Association, 2002.

Plisiene, et al., "Selective Transvascular Stimulation of Cardiac Autonomic Nerves: A Novel Technique", Biomedicine, Vo. 2, No. 1, Jul. 2002.

* cited by examiner

FIG. 5
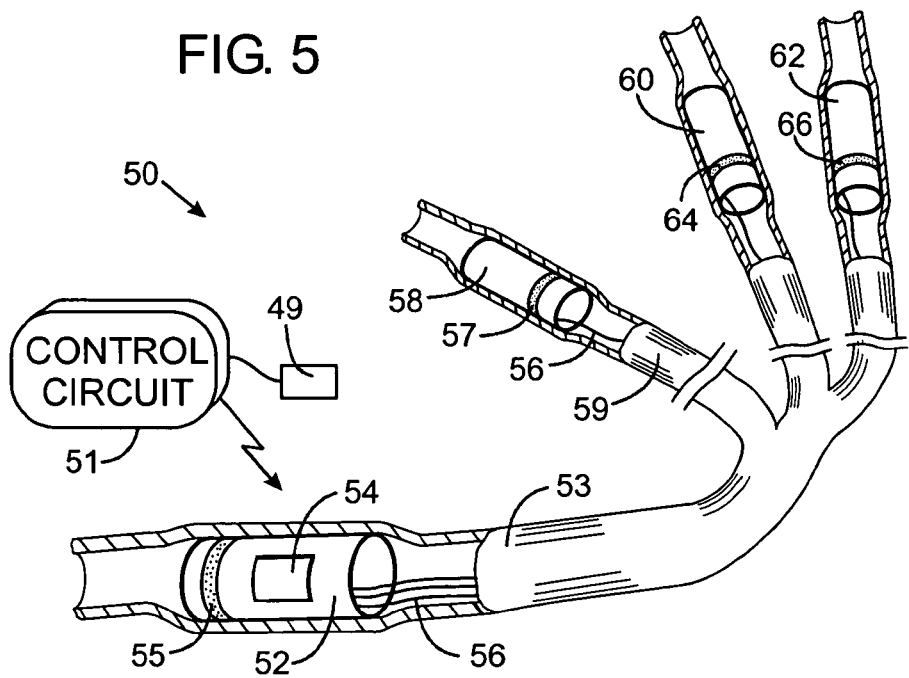
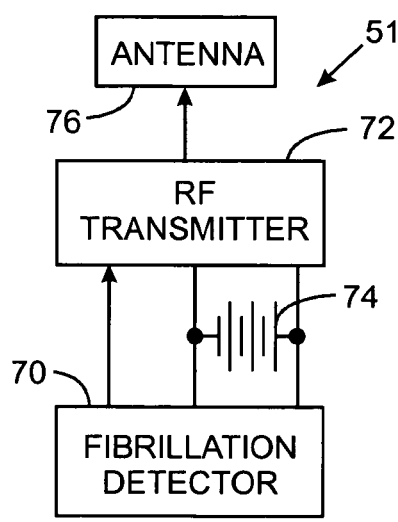
FIG. 6
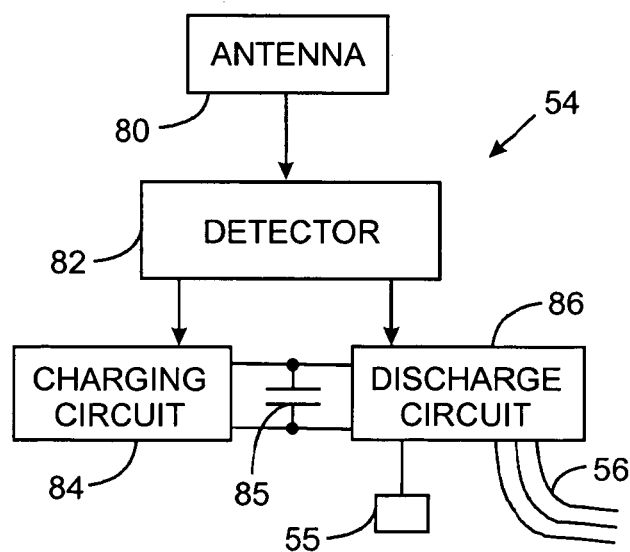
FIG. 7

VAGAL NERVE STIMULATION USING VASCULAR IMPLANTED DEVICES FOR TREATMENT OF ATRIAL FIBRILLATION

CROSS-REFERENCE TO RELATED APPLICATIONS

This application is a continuation in part of U.S. patent application Ser. No. 10/197,191 filed on Jul. 17, 2002, now U.S. Pat. No. 6,907,285, which is a continuation of Ser. No. 09/760,936 U.S. Pat. No. 6,445,953 that was filed on Jan. 16, 2001.

STATEMENT REGARDING FEDERALLY SPONSORED RESEARCH OR DEVELOPMENT

Not Applicable

BACKGROUND OF THE INVENTION

1. Field of the Invention

The present invention relates to implantable medical devices which deliver energy to cardiac tissue for the purpose of maintaining or producing a regular heart rate. Such devices are commonly referred to as cardiac pacing devices and defibrillators.

2. Description of the Related Art

A remedy for people with slowed or disrupted natural heart beating is to implant a cardiac pacing device. A cardiac pacing device is a small electronic apparatus that stimulates the heart to beat at regular rates. It includes a pulse generator, implanted in the patient's chest, which produces electrical pulses to stimulate heart contractions. Electrical leads extend from the pulse generator to electrodes placed adjacent to specific muscles of the heart, which when electrically stimulated produce contraction of the adjacent heart chambers.

Modern cardiac pacing devices adapt their pulse rate to adjust the heartbeats to the patient's level of activity, thereby mimicking the heart's natural beating. The pulse generator modifies that rate by tracking the activity at the sinus node of the heart or by responding to other sensors that monitor body motion and rate of breathing.

Different pacing needs are met by adjusting the programming of the pulse generator and by the location of the electrodes. It is quite common that the leads extend through blood vessels which enter the heart so that the electrodes can be placed in the muscle of the heart chamber requiring stimulation. This requires that the leads extend for some distance through the blood vessels and may necessitate that the leads pass through one or two heart valves. In other patients, patch electrodes are placed on the exterior heart surface with wires extending through tissue to the pacing device. With either type of lead placement, it is important that the electrodes be attached to the proper positions on the heart to stimulate the muscles and produce contractions. Thus it is desirable to properly locate the electrodes for maximum heart stimulation with minimal adverse impact to other physiological functions, such as blood circulation.

Other patients have hearts that occasionally go into fibrillation where the heart has very rapid shallow contractions and, in the case of ventricular fibrillation, may not pump a sufficient amount of blood to sustain life. Administration of a controlled electrical shock to the heart often is required to restore a normal rhythm. A defibrillator often is implanted in the chest cavity of a person who is susceptible to recurring episodes of ventricular fibrillation. Similar to a pacing device, the implanted defibrillator senses the rapid heart rate during fibrillation and applies a relatively high energy electrical pulse through wires connected to electrodes attached to the exterior wall of the heart or to leads in the heart chamber. The defibrillator generates a much more intense electrical pulse than is used by pacing devices which merely stimulate contractions of the heart.

A common heart condition is atrial fibrillation in which the upper chambers, the atria, of the heart quiver instead of beating effectively. Rapid atrial beating produces a corresponding rapid beating of the ventricles. Electrical cardioversion and drugs have been used to restore the heart's normal rhythm. Chronic atrial fibrillation, in which a normal rhythm could not be restored, is commonly treated with medication, such as beta blockers, to slow the rapid heart rate.

Scientific research on dogs discovered that transvenous parasympathic, or vagal nerve stimulation can be employed to slow the rapid ventricular rate induced by atrial fibrillation. In this treatment, an electrode at the tip of a catheter is fed through the blood vessels to a parasympathic nerve stimulation site in the inferior vena cava of the heart. During atrial fibrillation, electrical pulses were applied from an external source through a conductor in the catheter to the electrode, thereby stimulating the site in the inferior vena cava. Specific patterns of stimulation pulses slowed the ventricular rate.

SUMMARY OF THE INVENTION

An apparatus for stimulating a vagal nerve in an animal includes a power transmitter that emits a radio frequency signal. A stimulator, for implantation in a blood vessel adjacent the vagal nerve in the animal, has a pair of electrodes and an electrical circuit thereon. The electrical circuit receives the radio frequency signal and from the energy of that signal derives an electrical voltage. The electrical voltage is applied in the form of pulses to the pair of electrodes, thereby stimulating the vagal nerve.

In the preferred embodiment, the derived voltage is stored by a capacitor and a switch is periodically operated to apply the stored voltage across the pair of electrodes.

The vagal nerve stimulation apparatus can be combined into conventional implanted cardiac pacing or defibrillator devices.

BRIEF DESCRIPTION OF THE DRAWINGS

FIG. 5 illustrates a defibrillator that employs intravascular electrodes;

FIG. 6 is a block diagram of a control circuit for the circuit defibrillator in FIG. 5;

FIG. 7 is a block diagram of a pulsing circuit on a intravascular stimulator of the defibrillator;

DETAILED DESCRIPTION OF THE INVENTION

Figure 1:
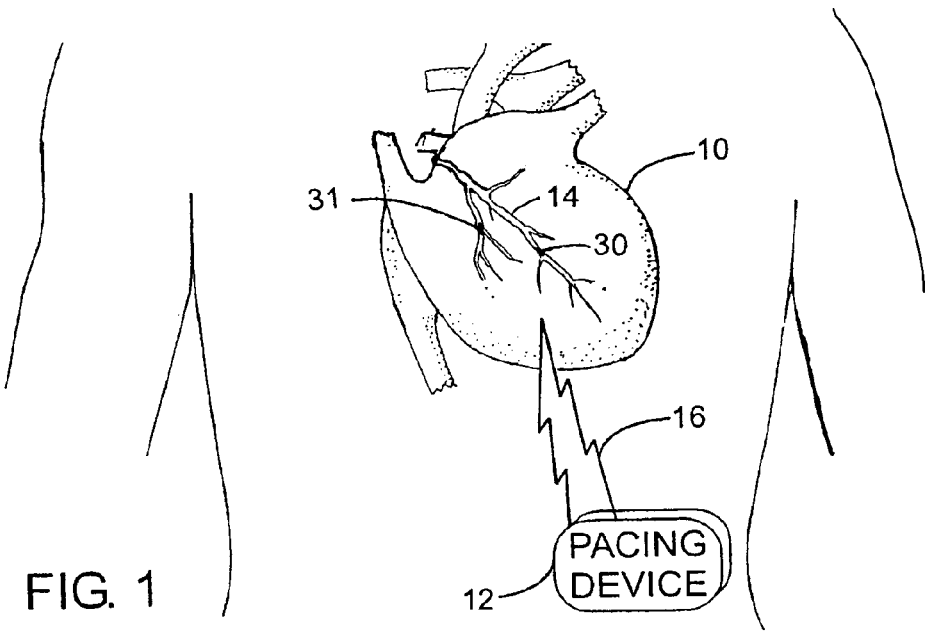
FIG. 1 is a representation of a cardiac pacing device implanted in a medical patient.

With initial reference to FIG. 1, an apparatus for applying electrical stimulation to pace a heart 10 comprises a pacing device 12 and one or more intravascular electrodes located in blood vessels, such as arteries 14, which supply blood to the heart muscles. As will be described in greater detail, the pacing device 12 emits a radio frequency signal 16 which produces an electric current in the implanted intravascular electrodes thereby stimulating the heart muscle.

Figure 2:
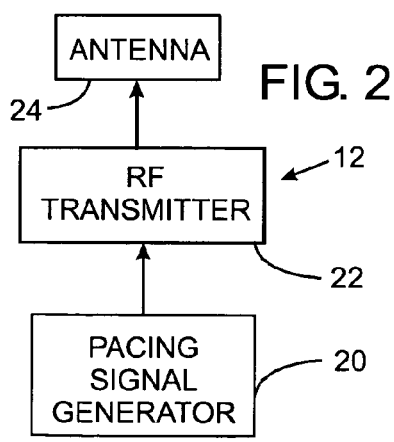
FIG. 2 is a block diagram of an electrical circuit for the pacing device in FIG. 1.

Referring to FIG. 2, the pacing device 12 comprises a conventional pacing signal generator 20 similar to that utilized in previous cardiac pacers that use electrodes connected to leads. The internal circuitry and operation of the pacing signal generator is similar to those prior cardiac pacers which detects irregular cardiac rates or rhythms and applies corrective electrical pulses to the heart. However, instead of the output stimulation signals being applied to the electrodes via leads, the pacing signals are applied to an input of a radio frequency (RF) transmitter 22. Both the pacing signal generator 20 and the RF transmitter 22 are powered by a battery (not shown). In response to the stimulation signal (also known as a pacing signal) from the generator 20, the radio frequency transmitter 22 generates a correspondingly long pulse of the radio frequency signal 16 that is transmitted throughout the chest cavity via an antenna 24. Preferably the antenna 24 either is located relatively close to the heart or is of a type which focuses the radio frequency signal toward the heart.

Figure 3:
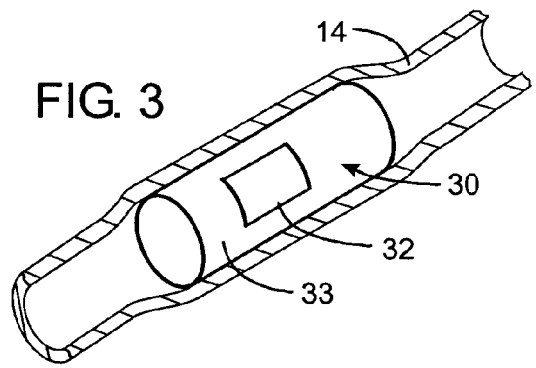
FIG. 3 is an isometric cut-away view of a cardiac blood vessel with a intravascular electrode implanted therein.

FIG. 3 illustrates an intravascular stimulator 30 that is placed in a blood vessel 14 of the heart 10. The body 33 of the intravascular stimulator 30 has a design similar to well-known expandable vascular stents that are employed to enlarge a restricted vein or artery. Such vascular stents have a generally tubular design that initially is collapsed to a relatively small diameter enabling them to pass freely through a blood vessel of a patient.

The procedure for implanting the intravascular stimulator 30 is similar to that used for conventional vascular stents. For example, the balloon at the end of a standard catheter is inserted into the intravascular stimulator 30 in a collapsed, or reduced diameter, configuration. That assembly then is inserted through an incision in a vein or artery near the skin of a patient and pushed through the vascular system to the appropriate location adjacent the heart 10. Specifically, the intravascular stimulator 30 ultimately is positioned in a cardiac blood vessel 14 adjacent to a section of the heart muscle where stimulation should be applied. The balloon of the catheter then is inflated to expand the intravascular stimulator 30, thereby slightly enlarging the blood vessel 14 which embeds the intravascular stimulator 30 in the wall of the vein or artery, as seen in FIG. 3. This slight enlargement of the blood vessel and the tubular design of the intravascular stimulator allows blood to flow relatively unimpeded through the device. The balloon is deflated, the catheter is removed from the patient, and the incision is closed. The intravascular stimulator 30 remains in the blood vessel without any wire connecting an electrode to pacing device 12. Alternatively a self expanding stimulator body may be utilized.

Figure 4:
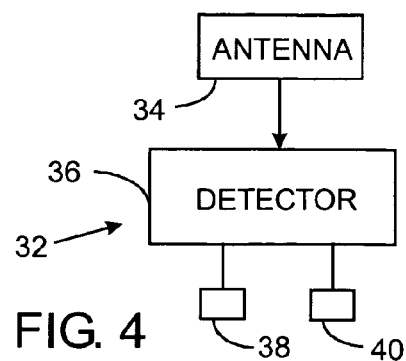
FIG. 4 is a block diagram of an electrical circuit on the intravascular electrode.

With reference to FIGS. 3 and 4, the intravascular stimulator 30 has a body 33 on which is mounted a signal receiving circuit 32. The signal receiving circuit 32 includes an antenna 34, a radio frequency signal detector 36, and a stimulator, that is formed by first and second electrodes 38 and 40, for example. The antenna 34 is connected to an input of the radio frequency signal detector 36. That detector is tuned to the frequency of the RF signal 16 that is emitted by the pacing device 12. Upon detecting the radio frequency signal 16, the detector 36 converts the energy of that signal into an electric current that is applied to the first and second electrodes 38 and 40. Those electrodes form an electric circuit path with the patient's heart tissue allowing for stimulation of that tissue. Thus, each time the pacing device 12 emits a radio frequency signal 16, a pulse of electrical current is produced in the vicinity of the intravascular stimulator 30, thereby stimulating the heart muscle adjacent to that electrode.

Therefore, instead of coupling the pacing device to the electrodes by wires extending through the vascular system and even the heart itself, the present invention employs radio frequency signals to provide that coupling. This eliminates the need for electrical leads that extend through the blood vessels which can break thus disabling the cardiac pacing. Furthermore, the present intravascular stimulators 30 and 31 can be located in the cardiac blood vessels 14 at points that are directly associated with the specific muscles requiring stimulation.

With reference to FIG. 1, a plurality of intravascular stimulators 30 and 31 which are tuned to the same radio frequency can be positioned in cardiac blood vessels at different locations in the heart to provide simultaneous stimulation of the adjacent tissue regions.

Alternatively, the plurality of intravascular stimulators 30 and 31, implanted in various veins or arteries of the heart muscle, can be tuned to different radio frequencies. In this embodiment, the radio frequency transmitter 22 also is tunable to produce output signals at several different radio frequencies, in response to an electrical control signal from the pacing signal generator 20. The pacing signal generator 20 now specifies the duration and the frequency of the RF signal 16 in order to select an intravascular stimulator to stimulate the heart muscle at a particular location. As a consequence, different portions of the heart muscle can be stimulated independently and sequentially by varying the radio frequency of the emitted RF signal 16 to correspond to the frequency to which the intravascular stimulator 30 in a given location is tuned. Furthermore, the plurality of intravascular stimulators 30 can be activated in a given sequence by producing a series of pacer signals at different radio frequencies. This enables the pacing device 12 to produce a sequential contraction of the heart chambers to increase cardiac efficiency.

Intravascular electrodes also can be employed with a cardiac defibrillator 50 as illustrated in FIG. 5. The defibrillator 50 has a control circuit 51 which detects fibrillation of the heart via sensor 49 and sends a radio frequency control signal to a intravascular stimulator 52 located in a vein or artery 53 in one section of the heart. The intravascular stimulator 52 includes an electronic circuit 54 and a first electrode 55. The electronic circuitry 54 is connected to a secondary intravascular electrode 58 by a conductor 56 in the form of a wire that extends through the vascular system. The secondary intravascular electrode 58 is located in another blood vessel 59 in a different section of the heart and has a second electrode 57 to which the conductor 56 is attached. Additional intravascular secondary electrodes 60 and 62 can be placed into other veins or arteries 59 of the heart. These secondary electrodes 60 and 62 have a structure identical to secondary intravascular electrode 58 with third and fourth electrodes 64 and 66 connected by wires to the intravascular stimulator 52. The intravascular stimulator 52 and the secondary electrodes 58, 60 and 62 are implanted using a procedure similar to that described previously for intravascular stimulator 30. The secondary intravascular electrodes 58, 60 and 62 may be significantly smaller that the intravascular stimulator 52 as they do not contain electronic circuitry, such as a charge storage capacitor as will be described. Thus the secondary intravascular electrodes can be placed in smaller blood vessels.

With reference to FIG. 6, the defibrillator control circuit 51 preferably is implanted in the chest of the patient, but may be worn externally in close proximity to the heart. The control circuit 51 has a fibrillation detector 70 which employs conventional techniques to detect an irregular heart rate and determine when a defibrillation pulse should be applied to the patient's heart. When that is to occur, the fibrillation detector 70 signals the radio frequency (RF) transmitter 72 to send a wireless signal via antenna 76 to the intravascular stimulator 52. The resultant radio frequency signal has greater energy than the signal from the pacing device 12 in FIG. 2 and thus provides sufficient energy to enable the intravascular stimulator 52 to deliver a more intense defibrillation pulse to the patient. A battery 74 provides power for the control circuit 51.

Referring to FIG. 7, the electronic circuit 54 on the intravascular stimulator 52 includes an antenna 80 for receiving the radio frequency signal from the control circuit 51. An RF detector 82 is tuned to the designated radio frequency and applies energy from the received signal to a charging circuit 84, that uses the signal energy to charge a capacitor 85. When the charge on the capacitor is sufficient to produce a defibrillation pulse, a discharge circuit 86 dumps the charge to the electrode 55 on the intravascular stimulator 52. The electrodes 57, 64 and 66 of the secondary intravascular electrodes 58, 60 and 62 are connected by wires to the intravascular stimulator 52 thereby providing a return path to complete an electrical circuit for the charge pulse. This action applies an electrical pulse across the first electrode 55 and the second, third and fourth electrodes 57, 64 and 66 which shocks the patient's heart to restore a normal cardiac rhythm. Employing a plurality of secondary intravascular electrodes 58, 60 and 62 to form a circuit to the intravascular stimulator electrode 55 provides a greater dispersion of the energy and avoids a local discharge.

The radio frequency signal from the control circuit 51 has a duration that is sufficient to charge the capacitor 85 to the level necessary to deliver the electrical defibrillation pulse. Alternatively, the control circuit 51 may periodically send a brief radio frequency signal to the electronic circuitry 54 on the intravascular stimulator 52. This signal does not cause the stimulator circuit to deliver a defibrillation pulse, but is used merely to maintain the requisite charge on the capacitor 85. This ensures that the capacitor 85 will be nearly fully charged when a defibrillation pulse is required and shortens the time between receipt of the defibrillation signal and delivery of an electrical pulse to the heart. In this latter case the RF transmitter 72 sends a specially encoded control signal when the patient requires defibrillation. The RF detector 82 responds to that encoded control signal by triggering the discharge circuit 86 to deliver the electrical defibrillation pulse.

In an alternative, the fibrillation detector 70, that determines when to stimulate the patient, can be incorporated into the electronic circuit 54 on the intravascular stimulator 52. In this case, the control circuit 51 outside the body merely transmits a radio frequency signal from which the intravascular stimulator 52 derives electrical power. That electrical power is used to energize the circuitry on the intravascular stimulator 52 and charge the capacitor for electrical stimulation.

Figure 8:
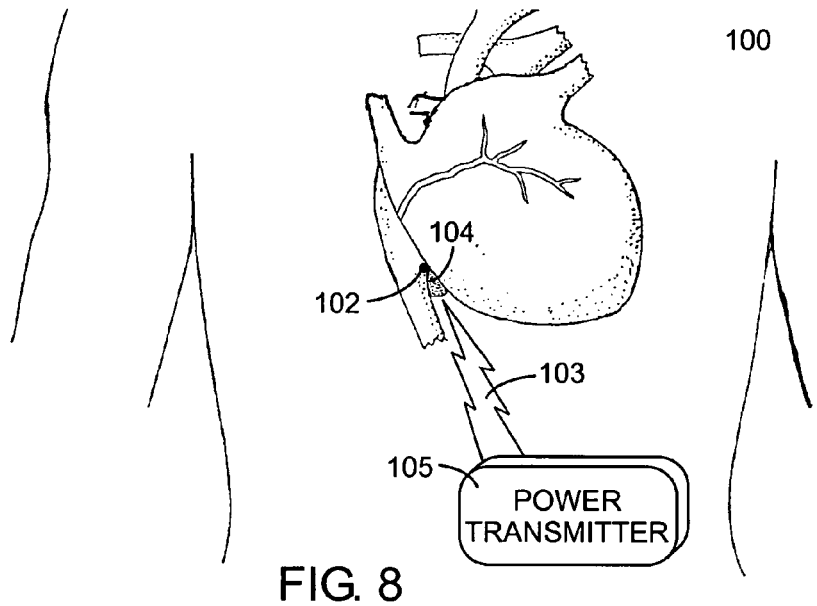
FIG. 8 is shows an intravascular vagal nerve stimulation apparatus for a medical patient.

An implanted intravascular stimulator according to the present design, can also be used to stimulate vagal nerves of the heart to slow rapid beating of the ventricles that results from atrial fibrillation. The heart has several places where a vagal nerve is close to a blood vessel, such as adjacent the inferior vena cava, the superior vena cava or the coronary sinus. As illustrated in FIG. 8, an apparatus 100 for treating atrial fibrillation has an intravascular stimulator 102 implanted at the inferior vena cava adjacent a fat pad containing a vagal nerve 104. The intravascular stimulator 102 receives a radio frequency (RF) signal 103 from a power transmitter 105 that is located outside the patient's body and is powered by a rechargeable battery. The energy of that RF signal 103 supplies power to the intravascular stimulator 102.

Figure 9:
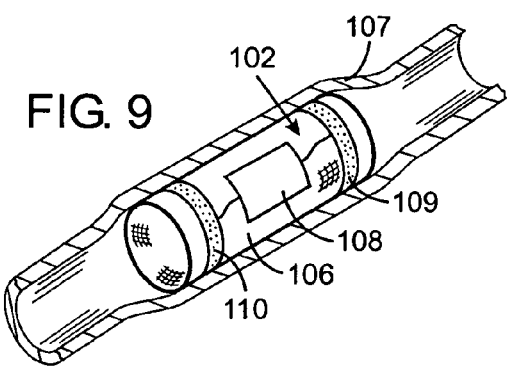
FIG. 9 is an isometric cut-away view of a blood vessel in which a vagal nerve stimulator is implanted.

With reference to FIG. 9, the intravascular stimulator 102 that is implanted in the inferior vena cava using the same technique described previously with respect to the other embodiments of intravascular stimulators. When properly positioned adjacent a vagal nerve, the body 106 of the intravascular stimulator 102 is expanded to become embedded in the wall of the blood vessel 107. The body 106 holds an electrical circuit 108 which is connected to first and second stimulation electrodes 109 and 110 that extend circumferentially around the intravascular stimulator 102 in contact with the wall of the blood vessel 107.

Figure 10:
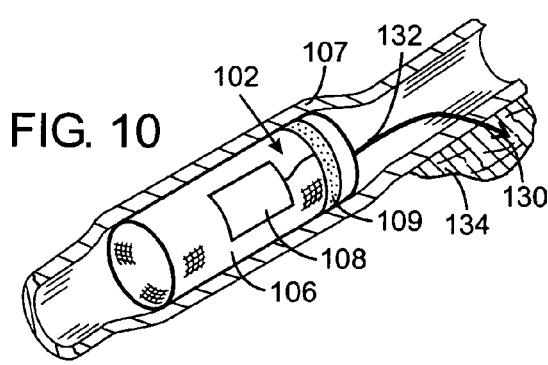
FIG. 10 is an isometric cut-away view of a blood vessel in which another version of the vagal nerve stimulator is implanted.
Figure 11:
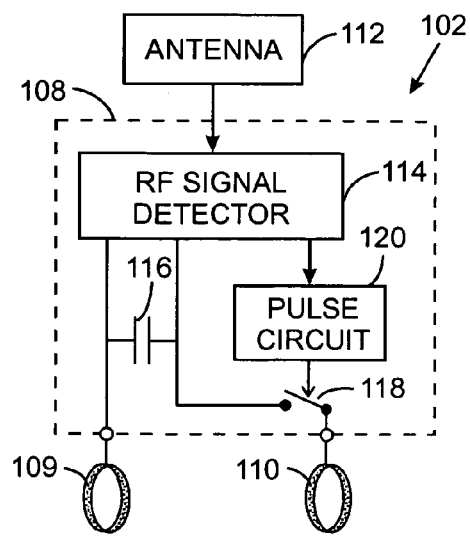
FIG. 11 is a block diagram of the electrical circuit in the vagal nerve stimulator.

Another embodiment of the intravascular stimulator 102, shown in FIG. 10, has only the first stimulation electrode 109 extending circumferentially around the body 106. A second stimulation electrode 130 is formed at a sharp tip of a lead 132 that perforates the wall of the blood vessel 107 and is embedded in the fat pad 134 containing a vagal nerve. With this version of the intravascular stimulator the electrical pulse is applied directly to the fat pad 134. The lead 132 may extend through the circulatory system to a different blood vessel than the one in which the body 106 is located in which case the device produces transvascular stimulation Referring to FIG. 11, the electrical circuit 108 is connected to a receive antenna 112 in the form of a wire coil wound circumferentially around the stimulator body 106. An RF signal detector 114 has an input connected to the receive antenna 112 and tuned to the frequency of the RF signal 103 that is emitted by the power transmitter 105. The RF signal detector 114 converts the energy of that RF signal into an electric voltage that charges a storage capacitor 116 which supplies electrical power to other components of the intravascular stimulator 102. Periodic pulses of the RF signal charge the storage capacitor 116 so that it will have sufficient stored energy when stimulation of the heart is required.

The first stimulation electrode 109 is connected to one terminal of the storage capacitor 116. The second stimulation electrode 110 is coupled by an electrically operated switch 118 to the other terminal of the storage capacitor 116. The switch 118 is controlled by a pulse circuit 120.

When the intravascular stimulator 102 receives the radio frequency signal 103 from the power transmitter 105, the RF signal detector 114 responds by activating the pulse circuit 120. Upon being activated the pulse circuit 42 periodically closes and opens the switch 118 to apply voltage pulses from the storage capacitor 116 across the first and second stimulation electrodes 109 and 110. That action completes a circuit thereby dumping applying stimulation voltage pulses to the vagal nerve that is adjacent those electrodes.

The power transmitter 105 may continuously transmit the RF signal 103 so that the stimulator always applies a voltage pulses to the vagal nerve to control the heart rate. Alternatively the power transmitter 105 can have circuitry similar to that of the pacing device 12 which detects abnormally rapid cardiac rates and responds by transmitting the RF signal 103 to produce vagal nerve stimulation. Furthermore, the stimulator also may have additional circuitry that performs conventional cardiac pacing in which case a remote electrode is located in another blood vessel of the heart and connected to the stimulator by an electrical conductor, such as electrode 57 and conductor 56 in FIG. 5. The pulse circuit 120 may also incorporate sensors so that the pattern of the stimulating pulses can be varied in response to characteristics of the atrial fibrillation.

In an alternative, the vagal nerve, intravascular stimulator 102 may be implemented with circuitry that detects when atrial fibrillation produces a significantly rapid heart rate that stimulation is required. In this case, the power transmitter 105 is located outside the body and merely transmits a radio frequency signal from which the intravascular stimulator 102 derives electrical power. That electrical power is used to energize the circuitry on the intravascular stimulator 102 and charge the capacitor 116 for electrical stimulation.

The foregoing description was primarily directed to a preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

We claim:

1. An apparatus for stimulating a vagal nerve in an animal, said apparatus comprising:
    a power transmitter that emits a radio frequency signal;
    a stimulator adapted for implantation inside a lumen of a blood vessel adjacent the vagal nerve in the animal and having a pair of electrodes and an electrical circuit, wherein the electrical circuit receives the radio frequency signal, derives an electrical voltage from energy of the radio frequency signal and applies the electrical voltage as pulses to the pair of electrodes thereby stimulating the vagal nerve.

2. The apparatus as recited in claim 1 wherein the stimulator comprises a tubular body having at least one of the pair of electrodes extending circumferentially there around.

3. The apparatus as recited in claim 2 wherein another one of the pair of electrodes is adapted to be embedded in tissue adjacent the vagal nerve and is connected to the electrical circuit by a lead that is adapted to extend through a wall of the blood vessel.

4. The apparatus as recited in claim 2 wherein the stimulator further comprises an antenna on the tubular body for receiving the radio frequency signal and connected to the electrical circuit.

5. The apparatus as recited in claim 1 wherein the electrical circuit comprises:
    a storage capacitor; and
    a radio frequency signal detector derives the electrical voltage from energy of the radio frequency signal and applies that voltage to the storage capacitor.

6. The apparatus as recited in claim 5 wherein the electrical circuit further comprises a pulse circuit that periodically causes application of voltage from the storage capacitor to the pair of electrodes.

7. The apparatus as recited in claim 5 wherein the electrical circuit further comprises:
    a switch which selectively connects at least one of the pair of electrodes to the storage capacitor; and
    a pulse circuit that periodically activates the switch to apply voltage from the storage capacitor across the pair of electrodes.

8. A method for stimulating a vagal nerve in an animal comprising:
    implanting a stimulator inside a lumen of a blood vessel adjacent the vagal nerve;
    transmitting a radio frequency signal from a power transmitter;
    receiving the radio frequency signal at the stimulator;
    deriving an electrical voltage from energy of the radio frequency signal received by the stimulator; and
    applying the electrical voltage as pulses to a pair of electrodes thereby stimulating the vagal nerve.

9. The method as recited in claim 8 wherein the vagal nerve is adjacent a heart of the animal and the applying the electrical voltage provides cardiac stimulation.

10. The method as recited in claim 8 further comprising storing the electrical voltage derived from energy of the radio frequency signal and then applying that stored electrical voltage as pulses to a pair of electrodes.

11. The method as recited in claim 10 wherein storing the electrical voltage comprises applying the electrical voltage to a storage capacitor at the stimulator.

12. The method as recited in claim 10 wherein applying the electrical voltage comprises periodically activating a switch through which that stored electrical voltage is applied to the pair of electrodes.

13. A method for treating atrial fibrillation in an animal comprising:
    implanting a stimulator inside a lumen of a blood vessel adjacent a vagal nerve of the animal;
    transmitting a radio frequency signal from a power transmitter;
    receiving the radio frequency signal at the stimulator;
    deriving an electrical voltage from energy of the radio frequency signal received by the stimulator; and
    applying the electrical voltage as pulses to a pair of electrodes thereby stimulating the vagal nerve.

14. The method as recited in claim 13 further comprising detecting a cardiac event produced by atrial fibrillation; and wherein applying the electrical voltage is in response to detecting the cardiac event.

15. The method as recited in claim 14 further comprising transmitting the radio frequency signal in response to detecting the cardiac event.

16. The method as recited in claim 13 further comprising storing the electrical voltage derived from energy of the radio frequency signal and then applying that stored electrical voltage as pulses to a pair of electrodes.

17. The method as recited in claim 16 wherein storing the electrical voltage comprises applying the electrical voltage to a storage capacitor at the stimulator.

* * * * *